(12) United States Patent
Miyachi

(10) Patent No.: US 10,143,444 B2
(45) Date of Patent: Dec. 4, 2018

(54) ULTRASONIC SIGNAL PROCESSING DEVICE AND ULTRASONIC SIGNAL PROCESSING METHOD

(71) Applicant: FUJIFILM Corporation, Tokyo (JP)

(72) Inventor: Yukiya Miyachi, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 888 days.

(21) Appl. No.: 14/537,613

(22) Filed: Nov. 10, 2014

(65) Prior Publication Data

US 2015/0065885 A1 Mar. 5, 2015

Related U.S. Application Data

(63) Continuation of application No. PCT/JP2013/063761, filed on May 17, 2013.

(30) Foreign Application Priority Data

May 25, 2012 (JP) ................................. 2012-119913

(51) Int. Cl.
*A61B 8/08* (2006.01)
*A61B 8/00* (2006.01)
(Continued)

(52) U.S. Cl.
CPC .......... *A61B 8/5207* (2013.01); *A61B 8/4444* (2013.01); *A61B 8/4483* (2013.01);
(Continued)

(58) Field of Classification Search
CPC .......... A61B 8/06; A61B 8/08; A61B 8/0891; A61B 8/4444; A61B 8/4483;
(Continued)

(56) References Cited

U.S. PATENT DOCUMENTS

2001/0037075 A1 * 11/2001 Candy ................ A61B 5/08
601/2
2010/0138191 A1 * 6/2010 Hamilton ........... G01S 15/8993
702/189
(Continued)

FOREIGN PATENT DOCUMENTS

JP 3-64607 U 6/1991
JP 4-44906 U 4/1992
(Continued)

OTHER PUBLICATIONS

Japanese Office Action dated Nov. 2, 2015, for Japanese Application No. 2012-119913, with a partial English translation.
(Continued)

*Primary Examiner* — Michael Rozanski
(74) *Attorney, Agent, or Firm* — Birch, Stewart, Kolasch & Birch, LLP

(57) ABSTRACT

An ultrasonic signal processing method includes: acquiring pieces of element data output from each element included in an ultrasonic probe including multiple elements configured to transmit an ultrasonic wave to a subject, receive an ultrasonic wave reflected by the subject and output an ultrasonic detection signal; determining element data to be preserved, according to depth information on a reception echo at an acquisition time of the element data, among the pieces of element data of each of the acquired elements; and preserving the element data determined to be preserved.

14 Claims, 11 Drawing Sheets

(51) Int. Cl.
*G01S 7/52* (2006.01)
*A61B 8/06* (2006.01)

(52) U.S. Cl.
CPC ........ *A61B 8/4494* (2013.01); *G01S 7/52049* (2013.01); *A61B 8/06* (2013.01); *A61B 8/08* (2013.01); *A61B 8/0891* (2013.01); *A61B 8/485* (2013.01)

(58) Field of Classification Search
CPC ..... A61B 8/4494; A61B 8/485; A61B 8/5207; G01S 7/52049
See application file for complete search history.

(56) References Cited

U.S. PATENT DOCUMENTS

2010/0145198 A1* 6/2010 Tsao .................... G01S 7/52047
600/447
2012/0323121 A1* 12/2012 Miller .................. A61B 8/4488
600/443

FOREIGN PATENT DOCUMENTS

| | | |
|---|---|---|
| JP | 7-303640 A | 11/1995 |
| JP | 11-164831 A | 6/1999 |
| JP | 2003-102730 A | 4/2003 |
| JP | 2005-279287 A | 10/2005 |

OTHER PUBLICATIONS

International Search Report, issued in PCT/JP2013/063761, dated Aug. 13, 2013.
Takao Higashiizumi, "Ultrasonic Diagnosis Apparatus: World of Ubiquitous Ultrasonic Waves that is increasingly expanding", [online], GE Healthcare Japan, [search on May 16, 2012], Internet, <URL: http://japan.gehealthcare.com/cwcjapan/static/rad/us/ubiquitous.html>.
Written Opinion of the International Searching Authority, issued in PCT/JP2013/063761, dated Aug. 13, 2013.
International Preliminary Report on Patentability and Written Opinion of the International Searching Authority together with English translations thereof, dated Dec. 4, 2014, for International Application No. PCT/JP2013/063761.

* cited by examiner

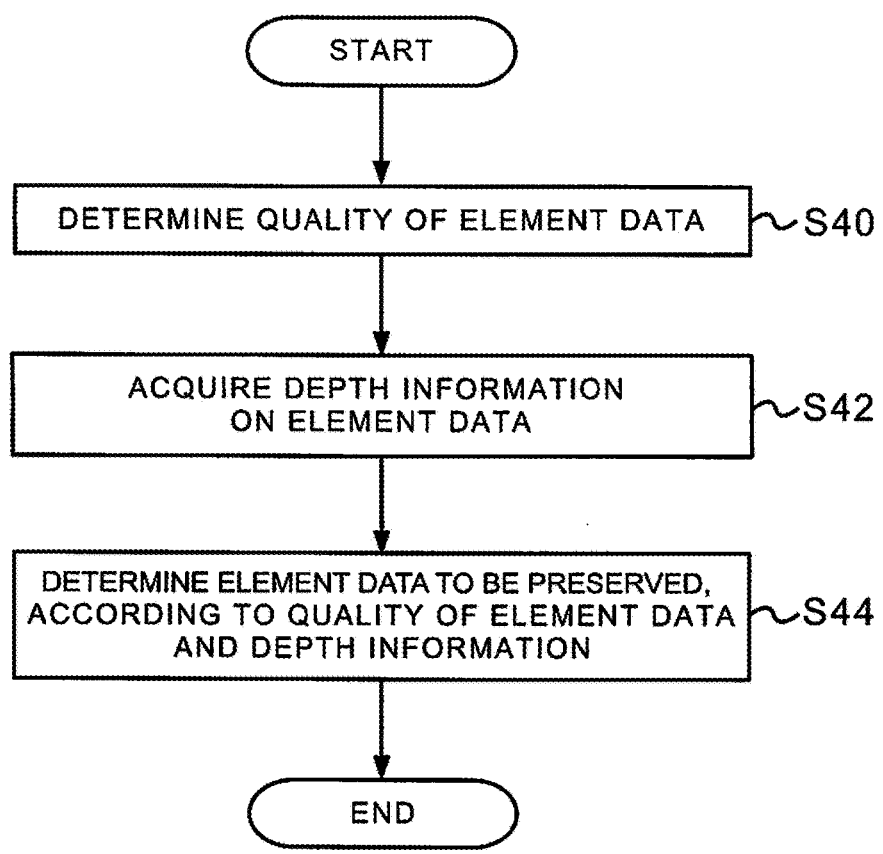

DEPTH

ULTRASONIC SIGNAL PROCESSING DEVICE AND ULTRASONIC SIGNAL PROCESSING METHOD

CROSS-REFERENCE TO RELATED APPLICATIONS

This application is a Continuation of PCT International Application No. PCT/JP2013/063761 filed on May 17, 2013, which claims priority under 35 U.S.C § 119(a) to Japanese Patent Application No. 2012-119913 filed on May 25, 2012. Each of the above applications is hereby expressly incorporated by reference, in their entirety, into the present application.

BACKGROUND OF THE INVENTION

Field of the Invention

The presently disclosed subject matter relates to an ultrasonic signal processing device and an ultrasonic signal processing method, and specifically relates to an ultrasonic signal processing device and an ultrasonic signal processing method that receive an ultrasonic echo reflected by a subject and record an ultrasonic signal.

Description of the Related Art

Japanese Patent Application Laid-Open No. H11-164831 (PTL 1) and Japanese Patent Application Laid-Open No. 2005-279287 (PTL 2) disclose that echo data 100 (raw data) by which ultrasonic image data is generated is recorded in a recording medium through predetermined processing (paragraphs [0006] and [0020] of PTL 1 and paragraphs [0007] and [0022] of PTL 2). Moreover, they disclose that search information 102A (for example, a patient ID, date and serial number, and so on) and attribute information 102B (for example, information showing transmission/reception conditions such as a transmission/reception mode, frequency, transmission and reception, transmission/reception rate and transmission/reception address; more specifically, an echo data blanking time between frames in a B mode and a blanking time every transmission in an M mode, and so on) are attached (paragraph [0018] of PTL 1 and paragraph [0020] of PTL 2).

Japanese Patent Application Laid-Open No. 2003-102730 (PTL 3) discloses that, when a signal subjected to an addition processing by an ultrasonic transmission/reception unit 14 is preserved as RF data (raw data), a resolution is changed between a designated region and other regions (paragraphs [0015] and [0020]).

Takao HIGASHIIZUMI, "Ultrasonic Diagnosis Apparatus: World of Ubiquitous Ultrasonic Waves that is increasingly expanding", [online], GE Healthcare Japan, [search on May 16, 2012], Internet, <URL: http://japan.gehealthcare.com/cwcjapan/static/rad/us/ubiquitous.html> (NPL 1) discloses a raw data management in which an image is stored as raw data which is data after a signal processing such as a reception focus in a beam former and before an image processing.

SUMMARY OF THE INVENTION

The raw data described in PTL 1 and PTL 2 denotes a digital reception signal acquired by an A/D conversion after a reception signal from a probe is detected. The raw data described in PTL 3 denotes RF data after the addition processing. Moreover, the raw data described in NPL 1 denotes raw data after a beam forming, that is, after a phase matching addition. Therefore, in the techniques described in PTL 1 to PTL 3 and NPL 1, there is a problem that it is not possible to hold element data useful for correction of a sound velocity in a subject and a creation of a sound velocity map, and so on.

Since element data before a beam forming has a larger amount of data than line data after the beam forming, a memory of huge capacity is required to record the element data. For example, in a case where data of 240 lines and a depth of 5 cm is taken in an ultrasonic signal processing device that records reception data with an amplitude of 2 bytes in which a number of reception channels is 64 ch and a sampling frequency is 40 MHz, an amount of line data after a beam forming is as follows:

2 (Byte)×0.05 (m)×2/1,540 (m/s)×40 (MHz)×240 (Line)=1.23 (MByte).

On the other hand, an amount of element data before the beam forming is as follows:

1.23 (MByte)×64 (ch)=78.72 (MByte).

For example, in a case where element data obtained by performing transmission focus on ten points is preserved to create a sound velocity map, an amount of the element data is as follows:

78.72 (MByte)×10 (point)=787.2 (MByte).

As described above, a memory capacity of about 1 (Giga Byte) is required whenever the element data for the sound velocity map is preserved once. Therefore, it is difficult to hold the element data before the beam forming.

The presently disclosed subject matter is made in view of such conditions, and it is an object to provide an ultrasonic signal processing device and an ultrasonic signal processing method that can hold element data before a beam forming.

To solve the above-mentioned problem, an ultrasonic signal processing device of the first mode of the presently disclosed subject matter includes: an ultrasonic probe including multiple elements configured to transmit an ultrasonic wave to a subject, receive an ultrasonic wave reflected by the subject and output an ultrasonic detection signal; an element data acquisition unit configured to acquire pieces of element data output from each element; a determination unit configured to determine element data to be preserved, according to depth information on a reception echo at an acquisition time of the element data, among the pieces of element data of each element acquired by the element data acquisition unit; and a preservation unit configured to preserve the element data determined to be preserved by the determination unit.

According to the first mode, a range of the element data to be preserved is limited based on the depth of the reception echo. By this means, it is possible to reduce a capacity of a memory required to preserve element data before a beam forming.

The ultrasonic signal processing device of the second mode of the presently disclosed subject matter is configured such that, in the first mode, the determination unit limits at least one of a numerical aperture of the element data to be preserved and a sample number in a depth direction of the element data to be preserved, according to the depth information on the reception echo at the acquisition time of the element data.

The ultrasonic signal processing device of the third mode of the presently disclosed subject matter is configured such that, in the first or second mode, the determination unit increases a numerical aperture of the element data to be preserved as a depth of the reception echo at the acquisition time of the element data becomes deeper.

The ultrasonic signal processing device of the fourth mode of the presently disclosed subject matter is configured such that, in the first to third modes, the determination unit sets a numerical aperture of the element data to be preserved such that an F value: F=L/x defined by a depth L of the reception echo and an aperture size x of the element data to be preserved becomes constant.

According to the third and fourth modes, by assuming element data suitable for reconfiguration of a B-mode image or the like as the element data to be preserved, it is possible to reduce the capacity of the memory required to preserve the element data before the beam forming.

The ultrasonic signal processing device of the fifth mode of the presently disclosed subject matter is configured such that, in the first to fourth modes, the determination unit decreases a sample number of the element data to be preserved as a depth of the reception echo at the acquisition time of the element data becomes deeper.

The ultrasonic signal processing device of the sixth mode of the presently disclosed subject matter is configured such that, in the first to fifth modes, the determination unit narrows a range in a depth direction of the element data to be preserved as a depth of the reception echo at the acquisition time of the element data becomes deeper.

According to the fifth and sixth modes, by limiting the sample number in the depth direction of the element data to be preserved or the range in the depth direction of the element data to be preserved, it is possible to reduce the capacity of the memory required to preserve the element data before the beam forming.

The ultrasonic signal processing device of the seventh mode of the presently disclosed subject matter is configured such that, in the first to sixth modes, the determination unit determines the element data to be preserved, according to waveforms of the pieces of element data acquired by the element data acquisition unit.

According to the seventh mode, element data in which the waveform of the ultrasonic reception signal greatly collapses (for example, element data by which a less-accurate image is generated or element data by which the sound velocity is less-accurately determined) is excluded from the element data to be preserved. By this means, it is possible to effectively reduce the capacity of a memory required to preserve element data before beam forming.

An ultrasonic signal processing method of the eighth mode of the presently disclosed subject matter includes: an element data acquisition step of acquiring pieces of element data output from each element included in an ultrasonic probe including multiple elements configured to transmit an ultrasonic wave to a subject, receive an ultrasonic wave reflected by the subject and output an ultrasonic detection signal; a determination step of determining element data to be preserved, according to depth information on a transmission focus position at an acquisition time of the element data, among the pieces of element data of each element acquired in the element data acquisition step; and a preservation step of preserving the element data determined to be preserved in the determination step.

The ultrasonic signal processing method of the ninth mode of the presently disclosed subject matter is configured such that, in the determination step of the eighth mode, at least one of a numerical aperture of the element data to be preserved and a sample number in a depth direction of the element data to be preserved is limited according to the depth information on the reception echo at the acquisition time of the element data.

The ultrasonic signal processing method of the tenth mode of the presently disclosed subject matter is configured such that, in the determination step of the eighth or ninth mode, a numerical aperture of the element data to be preserved is increased as a depth of the reception echo at the acquisition time of the element data becomes deeper.

The ultrasonic signal processing method of the eleventh mode of the presently disclosed subject matter is configured such that, in the determination step of the eighth to tenth modes, a numerical aperture of the element data to be preserved is set such that an F value: F=L/x defined by a depth L of the reception echo and an aperture size x of the element data to be preserved becomes constant.

The ultrasonic signal processing method of the twelfth mode of the presently disclosed subject matter is configured such that, in the determination step of the eighth to eleventh modes, a sample number of the element data to be preserved is decreased as a depth of the reception echo at the acquisition time of the element data becomes deeper.

The ultrasonic signal processing method of the thirteenth mode of the presently disclosed subject matter is configured such that, in the determination step of the eighth to twelfth modes, a range in a depth direction of the element data to be preserved is narrowed as a depth of the reception echo at the acquisition time of the element data becomes deeper.

The ultrasonic signal processing method of the fourteenth mode of the presently disclosed subject matter is configured such that, in the determination step of the eighth to thirteenth modes, the element data to be preserved is determined according to waveforms of the pieces of element data acquired in the element data acquisition step.

According to the presently disclosed subject matter, by limiting the range of the element data to be preserved according to the depth of the reception echo, it is possible to reduce the capacity of the memory required to preserve the element data before the beam forming.

BRIEF DESCRIPTION OF THE DRAWINGS

FIG. 9 is a flowchart showing the third embodiment of determination processing of the element data to be preserved;

DETAILED DESCRIPTION OF EXEMPLARY EMBODIMENTS

In the following, embodiments of an ultrasonic signal processing device and ultrasonic signal processing method according to the presently disclosed subject matter are described according to the accompanying drawings.

Configuration of Ultrasonic Signal Processing Device

Figure 1:
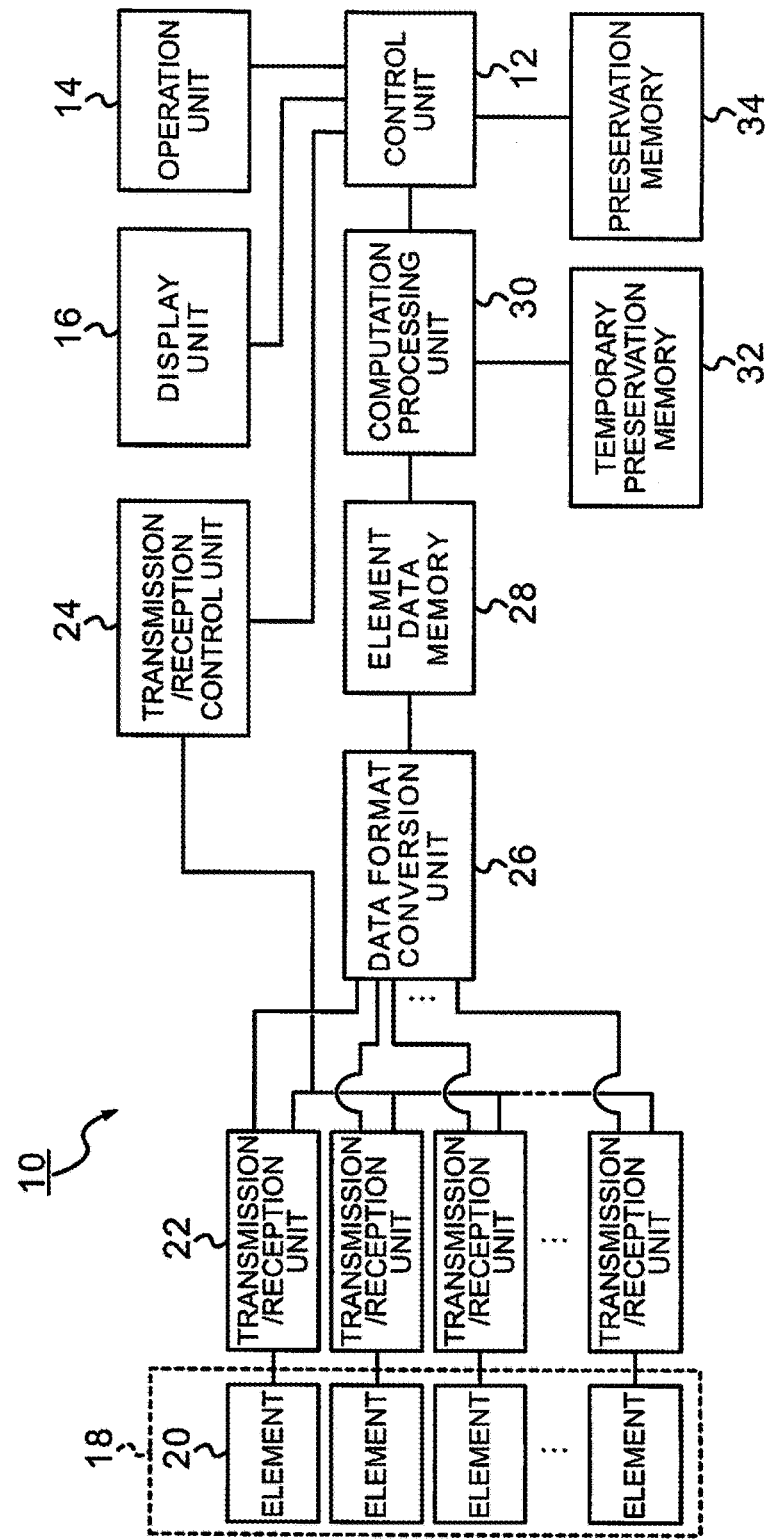
FIG. 1 is a block diagram illustrating an ultrasonic signal processing device according to an embodiment of the presently disclosed subject matter.

FIG. 1 is a block diagram illustrating an ultrasonic signal processing device according to an embodiment of the presently disclosed subject matter.

An ultrasonic signal processing device 10 illustrated in FIG. 1 is an apparatus that transmits an ultrasonic beam from an ultrasonic probe 18 to a subject OBJ, receives and records an ultrasonic echo reflected by the subject OBJ and creates/displays an ultrasonic image from a detection signal of the ultrasonic echo.

A control unit (processor for control) 12 performs control of each block of the ultrasonic signal processing device 10 according to an operation input from an operation unit 14. The control unit 12 includes a storage area that stores a control program to control each block of the ultrasonic signal processing device 10.

The operation unit 14 denotes an input device that accepts an operation input from an operator. The operation unit 14 includes a keyboard that accepts an input of character information (for example, patient information), and a pointing device (for example, a track ball, a mouse, a touch panel, or the like) that accepts an input of designating a region on a screen of a display unit 16. In addition, the operation unit 14 includes a display mode switching button that switches a display mode, a moving image playback button to instruct a moving image playback, and an analysis/measurement button to instruct analysis/measurement of an ultrasonic image.

The display unit 16 is, for example, a CRT (Cathode Ray Tube) display or a liquid crystal display. The display unit 16 displays an ultrasonic image (moving image and still image) and displays various setting screens.

The ultrasonic probe 18 is a probe used by being touched to the subject OBJ, and includes multiple ultrasonic transducers (elements) 20 forming a one-dimensional transducer array. The element 20 transmits an ultrasonic beam to the subject OBJ based on a driving signal applied from a transmission/reception control unit 24 through a transmission/reception unit 22. Further, the element 20 receives an ultrasonic echo reflected by the subject OBJ and outputs a detection signal (element data).

For example, the element 20 includes a vibrator configured such that electrodes are formed on both ends of a material (piezoelectric material) having piezoelectricity. As a piezoelectric material forming the above-mentioned vibrator, for example, it is possible to use a piezoelectric ceramic such as PZT (Pb (lead) zirconate titanate), and a polymer piezoelectric element such as PVDF (polyvinylidene difluoride). A piezoelectric material expands and contracts when a voltage is applied by transmitting an electrical signal to the electrodes of the above-mentioned vibrator, and an ultrasonic wave is generated in each vibrator by expansion and contraction of this piezoelectric material. For example, when a pulsed electrical signal is transmitted to the electrodes of the vibrator, a pulsed ultrasonic wave is generated. Moreover, when an electrical signal of continuous waves is transmitted to the electrodes of the vibrator, an ultrasonic wave of continuous waves is generated. Further, the ultrasonic wave generated in each vibrator is synthesized, and an ultrasonic beam is formed. Moreover, when an ultrasonic wave is received by each vibrator, the piezoelectric material of each vibrator expands and contracts to generate an electrical signal. The electrical signal generated in each vibrator is output to the transmission/reception unit 22 as an ultrasonic detection signal.

Here, as the ultrasonic transducer 20, it is also possible to use multiple different kinds of elements in an ultrasonic conversion scheme. For example, the vibrator configured by the above-mentioned piezoelectric material may be used as an element that transmits an ultrasonic wave, and an ultrasonic transducer (for example, Fabry-Perot resonator and fiber Bragg grating) of an optical detection scheme that converts an ultrasonic signal into an optical signal and detects it may be used as an element that receives the ultrasonic wave.

When the ultrasonic probe 18 touches a subject OBJ and an ultrasonic diagnosis starts by an instruction input from the operation unit 14, the control unit 12 outputs a control signal to the transmission/reception unit 22 and the transmission/reception control unit 24 and starts transmission of an ultrasonic beam to the subject OBJ and reception of an ultrasonic echo from the subject OBJ. The control unit 12 sets the transmission direction of the ultrasonic beam and the reception direction of the ultrasonic echo every element 20.

In addition, the control unit 12 selects a transmission delay pattern according to the transmission direction of the ultrasonic beam and selects a reception delay pattern according to the reception direction of the ultrasonic echo. Here, the transmission delay pattern is pattern data of a delay time given to a driving signal to form an ultrasonic beam in a desired direction with ultrasonic waves transmitted from multiple elements 20. Moreover, the reception delay pattern is pattern data of a delay time given to a detection signal to extract an ultrasonic echo from a desired direction by ultrasonic waves received by the multiple elements 20. The above-mentioned transmission delay patterns and reception delay patterns are stored in the control unit 12 beforehand. The control unit 12 selects a transmission delay pattern and a reception delay pattern from the ones stored beforehand. Further, the control unit 12 performs transmission/reception control of ultrasonic waves by outputting a control signal to the transmission/reception unit 22 according to the selected transmission delay pattern and reception delay pattern.

The transmission/reception control unit 24 generates a driving signal according to the control signal from the control unit 12 and applies the driving signal to the element 20 through the transmission/reception unit 22. At this time, the transmission/reception control unit 24 delays the driving signal applied to each element 20 according to the transmission delay pattern selected by the control unit 12 (transmission focus processing). Here, the transmission/reception control unit 24 adjusts (delays) the timing at which the driving signal is applied to each element 20 such that ultrasonic waves transmitted from the multiple elements 20 form an ultrasonic beam. Here, the timing at which the driving signal is applied may be adjusted such that the ultrasonic waves transmitted from the multiple elements 20 at a time reach the entire imaging region of the subject OBJ.

The transmission/reception unit 22 receives and amplifies the ultrasonic detection signal output from each element 20. Since the distance between each element 20 and an ultrasonic reflection source in the subject OBJ varies, the time at which a reflection wave reaches each element 20 varies. The transmission/reception unit 22 includes a delay circuit and delays each detection signal to the extent corresponding to the difference in the arrival time of the reflection wave (delay time), according to the sound velocity (assumption sound velocity) set based on the reception delay pattern selected by the control unit 12 or according to the distribution of the sound velocity.

A data format conversion unit 26 converts a parallel ultrasonic detection signal (element data) output from the transmission/reception unit 22 into serial element data (parallel-to-serial conversion). Moreover, the data format conversion unit 26 converts an analog ultrasonic detection signal (element data) output from the transmission/reception unit 22 into digital element data. Here, the data format conversion unit 26 may include a device such as FPGA (Field-Programmable Gate Array), and the data format conversion unit 26 can change the data format of the element data, and so on. The element data converted by the data format conversion unit 26 is temporarily preserved in an element data memory 28.

When the element data temporarily preserved in the element data memory 28 is transferred to a temporary preservation memory 32 and temporarily preserved therein, an computation processing unit (processor for calculation) 30 determines element data to be preserved. For example, the computation processing unit 30 determines a range of the element data to be preserved, according to depth information on the transmission focus position in the subject OBJ. The determination processing of the range of the element data to be preserved is described later.

Here, it is possible to use a volatile memory as the element data memory 28 and the temporary preservation memory 32. Here, the element data memory 28 and the temporary preservation memory 32 may be combinedly used as one memory.

A preservation memory 34 is, for example, a nonvolatile memory, and preserves element data determined to be preserved by the computation processing unit 30.

Here, the determination of the element data to be preserved may be performed by the computation processing unit 30 or the control unit 12 when element data is transferred from the temporary preservation memory 32 or the element data memory 28 to the preservation memory 34. Moreover, in a case where data format conversion is performed using a device such as FPGA as the data format conversion unit 26, the amount of element data that is transferred to the element data memory 28 and temporarily stored may be limited in the data format conversion unit 26 according to a control signal from the control unit 12.

In a case where the display mode is a live mode, the transmission/reception unit 22 performs reception focus processing by performing matching addition on the detection signal to which the delay time is given. For example, in a case where there is another ultrasonic reflection source in a position different from the ultrasonic reflection source in the subject OBJ, the arrival time is different in an ultrasonic detection signal from another ultrasonic reflection source. Therefore, the phase of the ultrasonic detection signal from another ultrasonic reflection source is negated by the matching addition in an addition circuit of the above-mentioned transmission/reception unit 22. By this means, the reception signal from the ultrasonic reflection source becomes largest, and the focus is adjusted to the above-mentioned ultrasonic reflection source. By the above-mentioned reception focus processing, an acoustic ray signal (hereinafter referred to as "RF signal") in which the focus of an ultrasonic echo is narrowed is formed.

An analog RF signal output from the transmission/reception unit 22 is converted into a digital RF signal (hereinafter referred to as "RF data"). Here, the RF data includes phase information on a reception wave (carrier wave). The above-mentioned RF data is input in the temporary preservation memory 32.

The temporary preservation memory 32 sequentially stores the above-mentioned RF data. Moreover, the temporary preservation memory 32 stores information on the frame rate input from the control unit 12 (for example, parameters showing the depth of an ultrasonic reflection position, the density of scanning lines, and the visual field width) in association with the above-mentioned RF data.

The computation processing unit 30 applies envelope detection processing to the above-mentioned RF data after attenuation by the distance is corrected according to the depth of the ultrasonic reflection position by STC (Sensitivity Time gain Control), and generates B-mode image data (image data showing the amplitude of an ultrasonic echo by spot luminance (brightness)). The above-mentioned B mode imaging data is acquired by a scanning scheme different from a scanning scheme for normal television signals. Therefore, the above-mentioned B mode imaging data is converted into normal image data (for example, image data of a television signal scanning scheme (NTSC (National Television System Committee) scheme) (raster conversion). After various kinds of necessary image processing (for example, gradation processing) is applied, the above-mentioned image data is converted into an analog image signal and output to the display unit 16. By this means, an ultrasonic image (moving image) taken by the ultrasonic probe 18 is displayed on the display unit 16.

Here, a detection signal to which the reception focus processing is applied in the transmission/reception unit 22 is assumed to be the RF signal in the present embodiment, but a detection signal to which the reception focus processing is not applied may be assumed to be the RF signal. In this case, the reception focus processing is digitally performed in the computation processing unit 30.

When the operation unit 14 accepts the input of the instruction of the moving image playback, the control unit 12 switches the operation mode of the ultrasonic signal processing device 10 to the moving image playback mode. At a moving image playback mode, the computation processing unit 30 reads out the RF data from the temporary preservation memory 32 according to an instruction from the control unit 12, applies predetermined processing (processing similar to that at the live mode) and converts it into image data. Further, the computation processing unit 30 converts the converted image data into an analog image signal and outputs it to the display unit 16. By this means, an ultrasonic image (moving image or still image) based on the RF data stored in the temporary preservation memory 32 is displayed on the display unit 16.

If a freeze instruction is input from the operation unit 14 when an ultrasonic image (moving image) is displayed at the live mode or the moving image playback mode, an ultrasonic image displayed when the freeze button is pressed is subjected to still image display in the display unit 16. By this means, the operator can display and observe the still image of Region of Interest (ROI).

When an analysis instruction is input form the operation unit 14, analysis and measurement designated by an operation input from the operator are performed. In a case where the analysis instruction is input, the computation processing unit 30 acquires RF data before image processing is applied, from the temporary preservation memory 32, and performs analysis/measurement (for example, strain analysis of an anatomy (hardness diagnosis), measurement of a blood flow, movement measurement of the organization part or IMT (Intima-Media Thickness) value measurement) designated by the operator using the RF data. This analysis/measurement result can be inserted in image data of the ultrasonic image and output to the display unit 16.

The computation processing unit 30 calculates an optimal sound velocity value in the region of interest ROI in the subject OBJ. When reception focus is performed for the region of interest ROI, for example, in a B-mode image, the optimal sound velocity value in the region of interest ROI in the subject OBJ can be calculated as a sound velocity value in which at least one of the contrast and sharpness of an image in the region of interest (transmission focus position) becomes highest. Moreover, based on the optimal sound velocity value in each transmission focus position calculated in this way, it is possible to correct the sound velocity in the subject OBJ and calculate a local sound velocity value in each transmission focus position by the computation processing unit 30 (for example, Japanese Patent Application Laid-Open No. 2010-099452).

Moreover, when an instruction of display mode switching is input, for example, the display mode is switched among a mode to display a B-mode image alone, a mode to superimpose and display a determination result of a local sound velocity value over the B-mode image (for example, display in which color classification or brightness is changed according to the local sound velocity value or display in which points of the identical local sound velocity value are connected by a line) and a mode to display the B-mode image and an image of the determination result of the local sound velocity value in a tiled manner. By this means, for example, the operator can discover a lesion by observing the determination result of the local sound velocity value.

Flow of Ultrasonic Signal Processing

Figure 2:
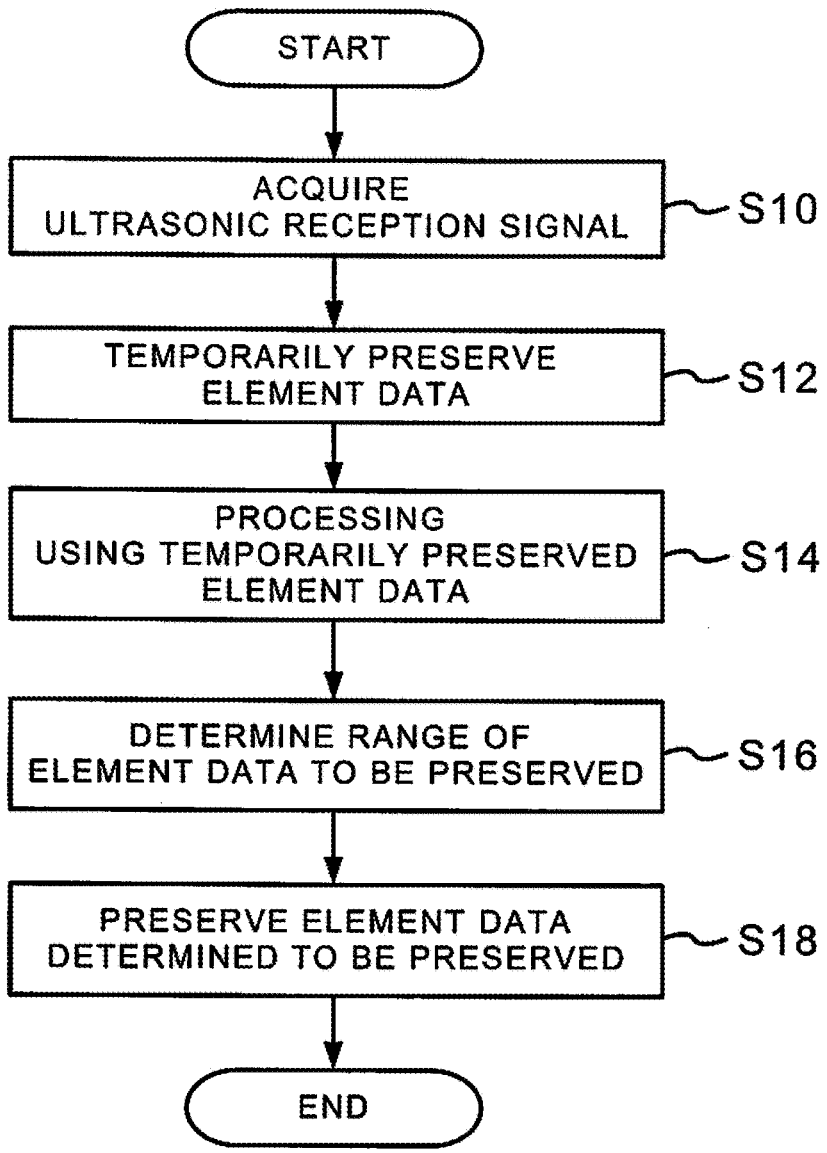
FIG. 2 is a flowchart showing a flow of processing of an ultrasonic signal processing method according to the embodiment of the presently disclosed subject matter.

FIG. 2 is a flowchart showing a flow of processing in an ultrasonic signal processing method according to an embodiment of the presently disclosed subject matter.

First, an ultrasonic beam is transmitted from the ultrasonic probe 18 into a subject OBJ and an ultrasonic echo reflected from the inside of the subject OBJ is received by the ultrasonic probe 18. By this means, an ultrasonic reception signal is acquired (step S10). This ultrasonic reception signal is output from the transmission/reception unit 22 as a parallel ultrasonic reception signal and converted into serial element data by the data format conversion unit 26. Further, this serial element data is input in the element data memory 28 and temporarily preserved together with depth information on the transmission focus position of the above-mentioned ultrasonic beam (step S12). Further, the temporarily preserved element data is transferred to the computation processing unit 30, and various kinds of processing such as the generation and display of a (B mode) image and a determination of sound velocity are performed (step S14).

Moreover, a range of element data to be preserved (at least one of the numerical aperture (channel number) and the sample number) is determined by the computation processing unit 30 according to depth information on a reception echo (step S16). The determination processing of a preservation object in step S16 is described later. Further, element data determined to be preserved is transferred to the preservation memory 34 and preserved therein (step S18).

First Embodiment of Determination Processing of Element Data to be Preserved

Figure 3:
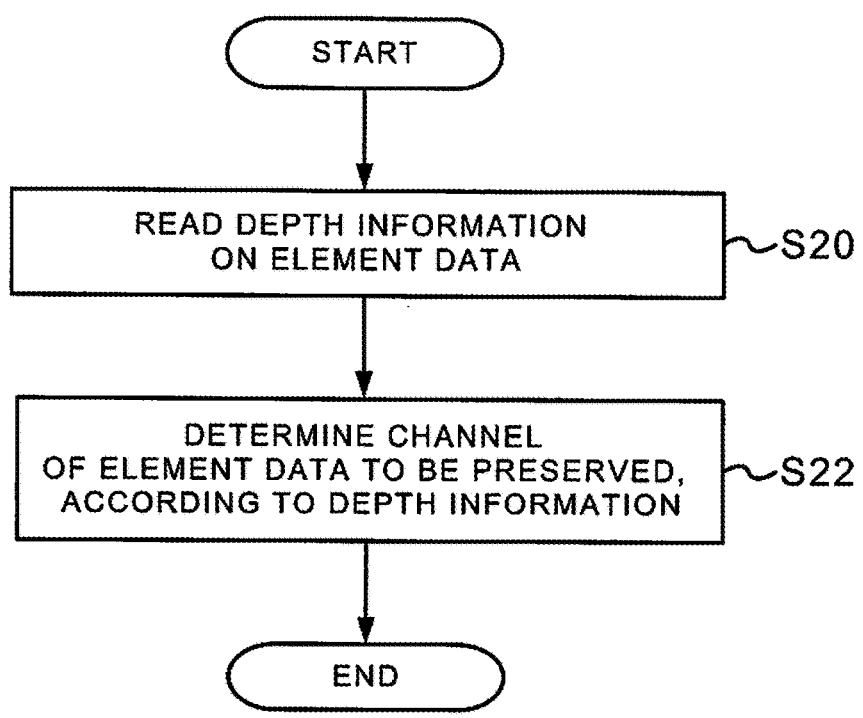
FIG. 3 is a flowchart showing the first embodiment of a determination processing of element data to be preserved.

FIG. 3 is a flowchart showing the first embodiment of determination processing of element data to be preserved (step S16).

First, the computation processing unit 30 reads depth information on a reception echo when the element data temporarily preserved in step S12 is acquired (step S20).

Next, the computation processing unit 30 determines a numerical aperture and position of element data to be preserved according to the above-mentioned depth information (step S22).

The processing in FIGS. 2 and 3 is repeatedly performed on multiple positions in the subject OBJ to acquire an ultrasonic echo every two-dimensional position of the reception echo. By this means, element data determined to be preserved is preserved in the preservation memory 34. The element data to be preserved is preserved in the preservation memory 34 together with, for example, information on the subject OBJ (for example, identification information on the subject OBJ (patient) and a preservation time and date of element data, or the like) and information on transmission/reception conditions of ultrasonic waves (for example, a transmission/reception mode, frequency, transmission/reception rate, transmission/reception address, coordinates and depth information of a transmission focus position corresponding to each element data, or the like).

Figure 4:
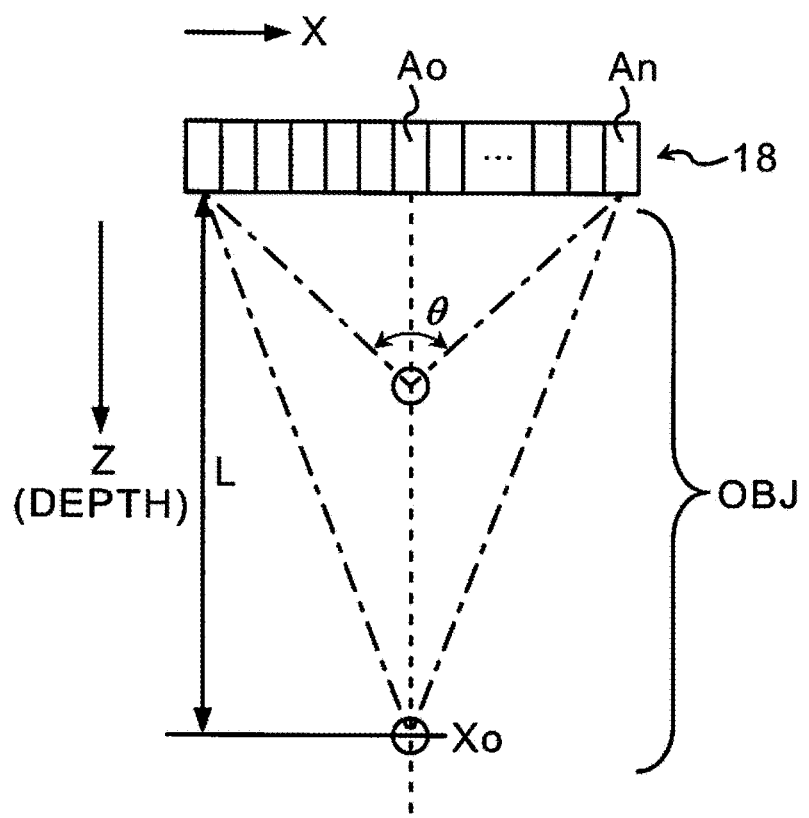
FIG. 4 is a diagram to describe a determination method of a numerical aperture (channel number) of the element data to be preserved.

FIG. 4 is a diagram to describe a determination method of the numerical aperture (channel number) of the element data to be preserved. In FIG. 4, an X axis shows an array direction of the ultrasonic transducer (element) 20 and a Z axis shows an ultrasonic propagation time corresponding to a depth direction or a depth in of the subject OBJ.

The strength of an ultrasonic reception signal becomes stronger as the position in the depth direction of a transmission focus position becomes shallower (closer to an ultrasonic probe or closer to the −Z side), and it becomes weaker as it becomes deeper (more distant from the ultrasonic probe or closer to the +Z side). Meanwhile, as illustrated in FIG. 4, in a case where the position in the depth direction of the transmission focus position is shallower, a scattering angle θ of an ultrasonic echo received in an element An positioned in the edge of the ultrasonic probe 18 become larger. Therefore, noise included in an ultrasonic reception signal increases. Therefore, in the determination of the numerical aperture of the above-mentioned element data to be preserved, the numerical aperture of the element data to be preserved is determined to be smaller as the position in the depth direction of a reception echo becomes shallower, and determined to be larger as it becomes deeper. Moreover, for example, the channels of element data to be preserved is equally distributed in the ±X direction with respect to an element Ao as a center in a position (position of same X-coordinate) immediately below transmission focus position Xo at the acquisition time of the element data (the same number of channels is distributed in the ±X direction with respect to the element Ao as the center).

As described above, in the present embodiment, the numerical aperture (a size of an aperture) of the element data to be preserved is increased according to the increase in the scan depth. By this means, the resolution in the azimuth direction of the entire image can be kept uniform. For example, a reception aperture may be changed while reception F value (=(depth L of a received echo)/(numerical reception aperture (or a size of the aperture) X)) is kept about 2.

In the present embodiment, the channels of the element data to be preserved may be limited to the ones used to generate an image (B-mode image). For example, when element data corresponding to all channels temporarily preserved in the element data memory 28 is preserved in the preservation memory 34, element data outside a reception aperture decided according to the reception F value is not subject to a preservation object. By this means, it is possible to compress the data amount of the element data to be preserved. Moreover, it is possible to reconfigure element data required to create a B mode image, or the like, by preserving the reception F value or the numerical reception aperture in each depth in attachment information on the element data to be preserved (for example, information on a header part of the element data).

Figure 5:
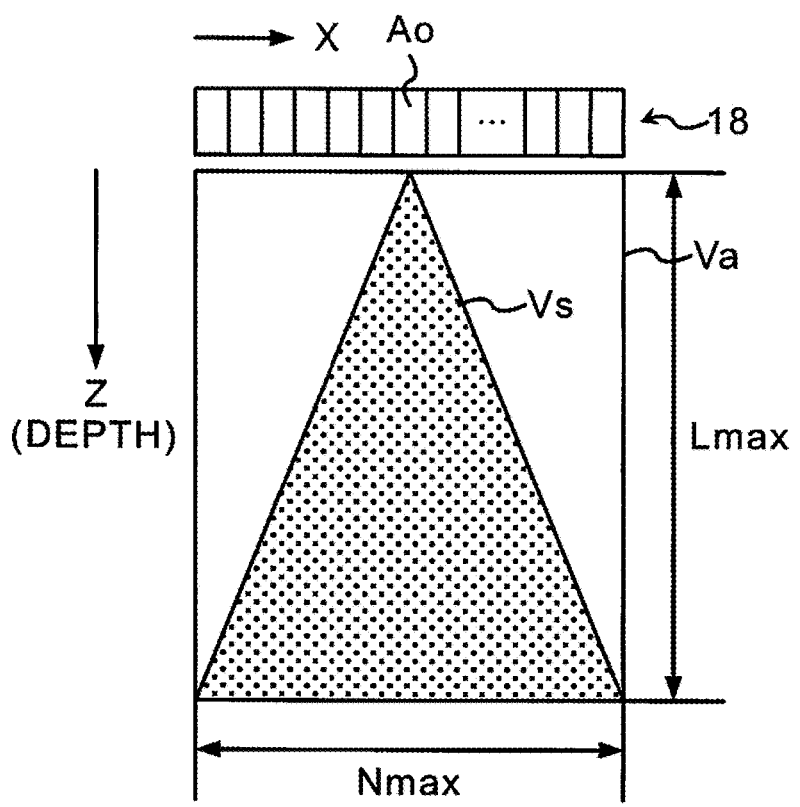
FIG. 5 is a diagram schematically illustrating a relationship between the numerical aperture (channel number) of the element data to be preserved and a depth of a region of interest.

FIG. 5 is a diagram schematically illustrating the relationship between the numerical aperture (channel number) of the element data to be preserved and the depth of the region of interest. In FIG. 5, an X axis shows the channel position (scan direction) channel of the element data and a Z axis shows the ultrasonic reception time corresponding to the depth direction or the depth of the subject OBJ.

The determination criterion of the element data to be preserved is assumed to be F=2, and it is designed such that the numerical aperture (channel number) of the element data to be preserved becomes a maximum value Nmax in the deepest region (maximum depth Lmax) in a region in which an ultrasonic beam is scanned. In FIG. 5, element data of all channels (numerical aperture Nmax) is shown by a rectangle region Va. Further, the data amount of the element data of all channels is shown by the area of the rectangle region Va (Lmax×Nmax).

Meanwhile, the element data to be preserved is shown by a region Vs of a substantially triangle shape or trapezoidal shape in which the width in the X direction narrows toward an element Ao immediately below a position Xo of the reflection source of an ultrasonic echo (reception echo) when the above-mentioned element data is acquired. Further, the data amount of the element data to be preserved is shown by the area of the region Vs.

Therefore, by assuming element data outside a channel (opening) decided by F=2 not to be subject to the preservation object, the data amount of the element data to be preserved is reduced to around half of the data amount (Lmax×Nmax) of the element data of all channels.

Figure 6:
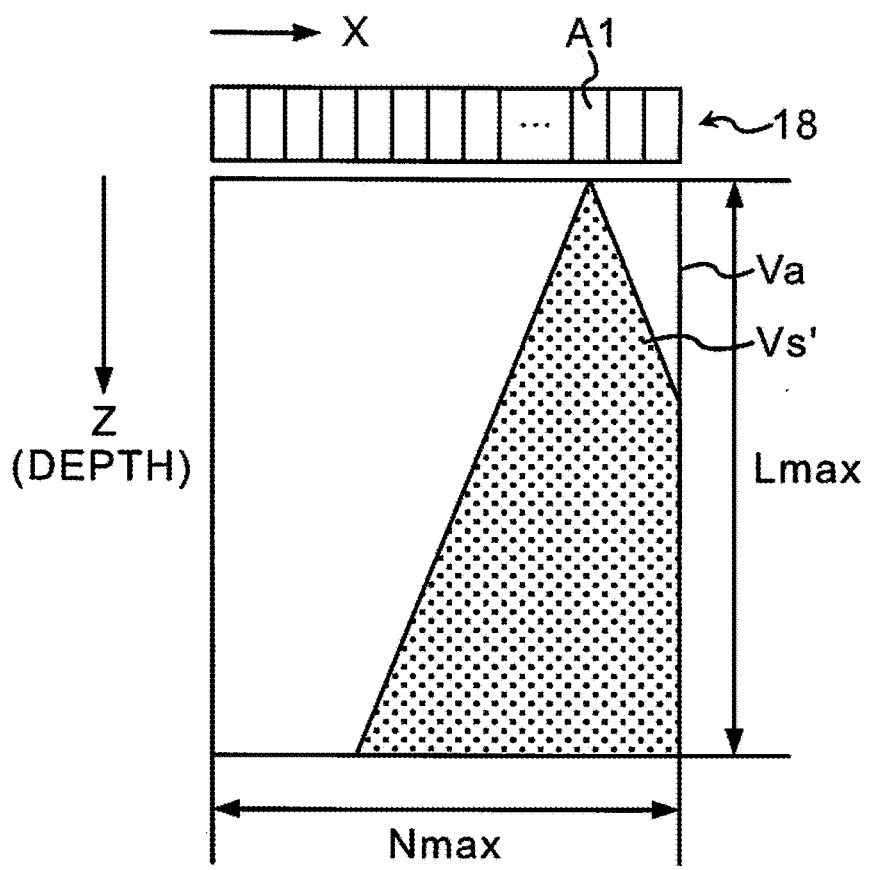
FIG. 6 is a diagram schematically illustrating the relationship between the numerical aperture (channel number) of the element data to be preserved and the depth of the region of interest.

FIG. 6 shows an example in which the position of the reflection source of the ultrasonic echo (reception echo) is near the edge of the ultrasonic probe 18. In the example illustrated in FIG. 6, the element data to be preserved is shown by a region Vs' which is a partial region of an isosceles triangle shape having a base length of Nmax and a vertex near element A1 immediately below position Xo of the reflection source of an ultrasonic echo (reception echo) and which is included in rectangle region Va corresponding to a scan range.

According to the present embodiment, the range of element data to be preserved is limited according to the depth of a reception echo and the numerical aperture (channel number). By this means, it is possible to reduce the capacity of a memory required to preserve element data before beam forming. In addition, according to the present embodiment, since it is possible to preserve the element data before beam forming with lower capacity, it becomes possible to process the preserved element data again to create and analyze a desired image such as a B-mode image and determine the sound velocity value (local sound velocity value) and the optimal sound velocity value (for example, a sound velocity value in which at least one of the contrast and sharpness of an image in a transmission focus position becomes highest in a B-mode image) on an arbitrary transmission focus position in the subject OBJ.

Second Embodiment of Determination Processing of Element Data to be Preserved

The present embodiment is designed such that the range of the element data to be preserved is limited according to the sample number in the depth direction.

Figure 7:
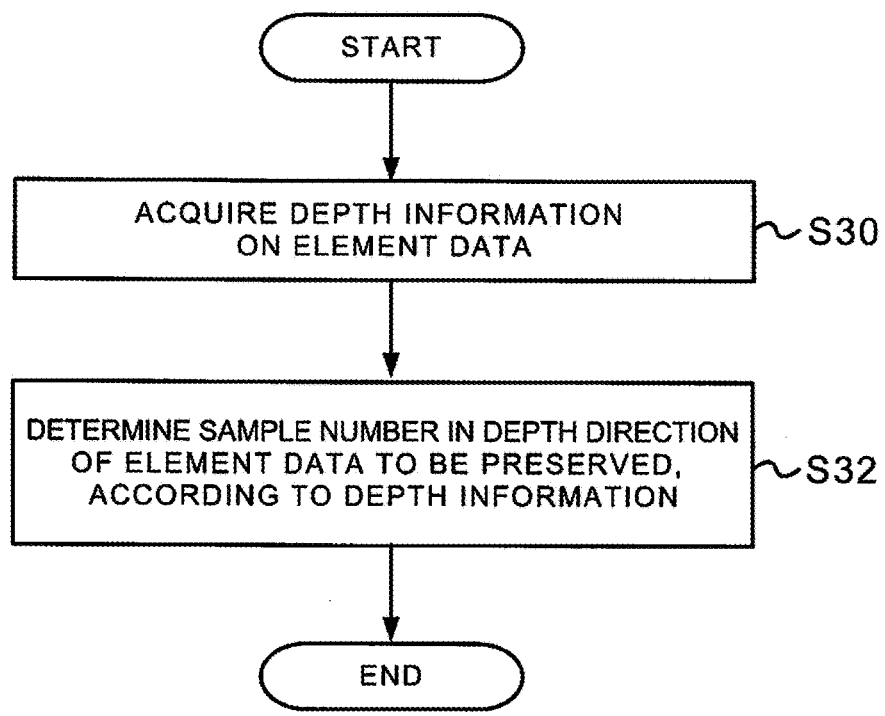
FIG. 7 is a flowchart showing the second embodiment of a determination processing of the element data to be preserved.

FIG. 7 is a flowchart showing the second embodiment of determination processing of element data to be preserved.

First, the computation processing unit 30 reads depth information on a transmission focus position when the element data temporarily preserved in step S12 is acquired (step S30).

Next, the computation processing unit 30 determines the range (sample number) in the depth direction of the element data to be preserved according to the above-mentioned depth information (step S32).

The processing in FIG. 7 is repeatedly performed every transmission focus position (every region of interest) in a subject OBJ. By this means, it is possible to preserve element data before beam forming corresponding to each transmission focus position.

Figure 8:
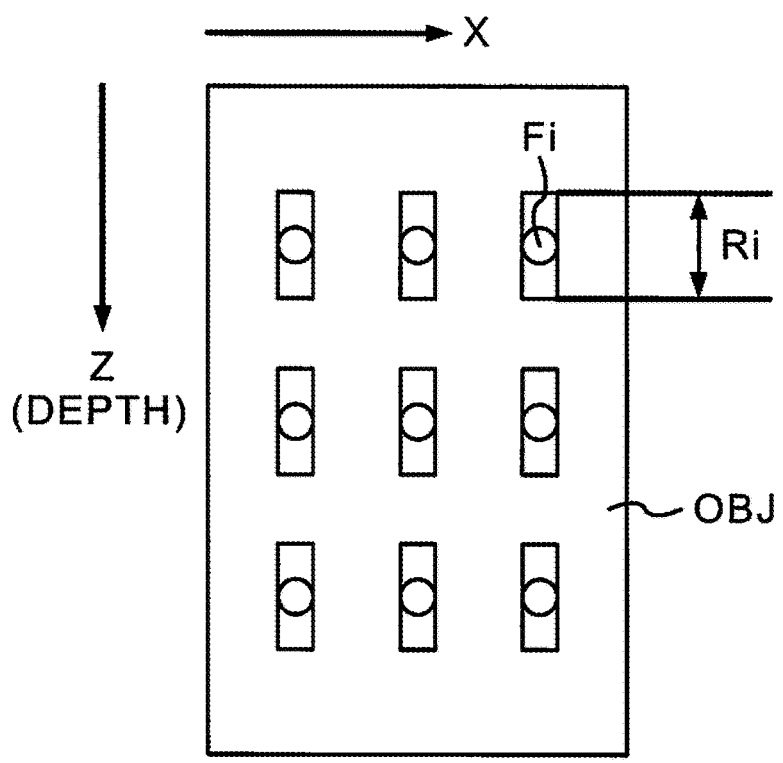
FIG. 8 is a diagram schematically illustrating a relationship between a sample number of the element data to be preserved and the depth of the region of interest.

FIG. 8 is a diagram schematically illustrating a relationship between a sample number of the element data to be preserved and a depth of a region of interest. In FIG. 8, an X axis shows a channel position (scan direction) of the element data and a Z axis shows an ultrasonic reception time corresponding to a depth direction or the depth of the subject OBJ.

In the present embodiment, the range in the depth direction (Z direction) of a preservation object in element data acquired at the time of calculation of the above-mentioned optimal sound velocity value is limited. Specifically, as the depth of a transmission focus position (or reception echo position) Fi becomes shallower (or closer to the −Z side), the sample number of element data is increased (range Ri in the depth direction in which element data is acquired is widened). On the other hand, as the depth of the transmission focus position Fi becomes deeper (or closer to the +Z side), the sample number of element data is decreased (range Ri in the depth direction in which element data is acquired is narrowed). Here, the range of the element data to be preserved may be limited to a periphery or an adjacent region of the transmission focus position Fi.

According to the present embodiment, by limiting the sample number in the depth direction of the element data to be preserved, it is possible to reduce the capacity of a memory required to preserve element data before beam forming.

By using the element data preserved in the preservation memory 34 as described above, for example, it is possible to determine and correct the optimal sound velocity value and the local sound velocity value and create a sound velocity map in which the sound velocity value is shown by color variation or gray scale.

Here, it is also possible to preserve the above-mentioned element data to be preserved and B-mode image data generated in step S14 of FIG. 2 or element data thinned out for creating an B-mode image, in the preservation memory 34 in association with each other. By this means, it is possible to perform processing of superimposing and displaying an image showing sound velocity assumed to be preserved in the present embodiment over the above-mentioned B mode image data, and so on.

Third Embodiment of Determination Processing of Element Data to be Preserved

In the present embodiment, a quality of element data is determined every transmission focus position, and, according to a determination result of the above-mentioned quality, element data to be determined is determined.

FIG. 9 is a flowchart showing the third embodiment of determination processing of element data to be preserved.

First, a quality of element data is determined (step S40). For example, the determination of the quality of the element data is performed according to collapse of a waveform of an ultrasonic reception signal. In step S40, the computation processing unit 30 calculates a parameter showing the quality of the element data. Here, the parameter showing the quality of the element data may include, for example, a difference between a waveform of an ultrasonic beam transmitted when the element data is acquired and a waveform of an ultrasonic reception signal after the reception focus or phase matching addition of the element data, an absolute value of the above-mentioned difference, an integral value in a predetermined time of the above-mentioned difference or the absolute value of the difference, or a value obtained by normalizing these. In a case where the parameter of the above-mentioned quality is equal to or greater than a threshold, the computation processing unit 30 determines that the quality of the element data is low, and, in a case where the parameter of the above-mentioned quality is less than the threshold, determines that the quality of the element data is high.

Next, the computation processing unit 30 reads depth information on a transmission focus position when the element data temporarily preserved in step S12 is acquired (step S42).

Next, the computation processing unit 30 excludes element data determined to be low quality from a preservation object according to the information on the quality of the above-mentioned element data. Further, similar to the above-mentioned second embodiment, the computation processing unit 30 determines the range (sample number) in the depth direction of element data to be preserved according to the depth information acquired in above-mentioned step S42, in element data determined to be high quality (step S44).

Here, a correlation value calculating the correlation between element data and a parabola may be used as the parameter showing the quality of the element data in step S40.

Figure 10A:
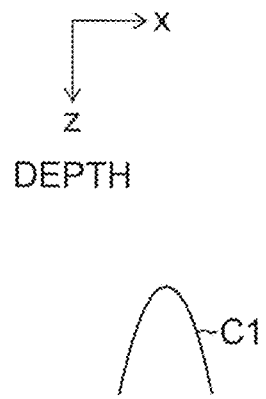
FIG. 10A is a diagram to describe a determination method of a quality of the element data.
Figure 10B:
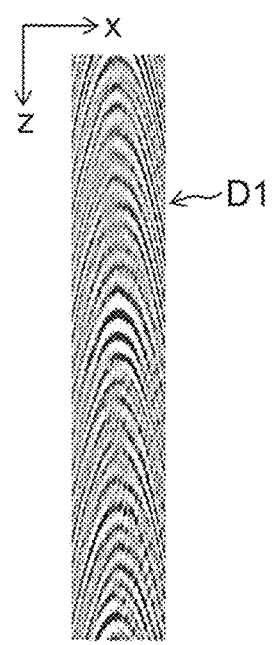
FIG. 10B is a diagram to describe a determination method of the quality of the element data.
Figure 10C:
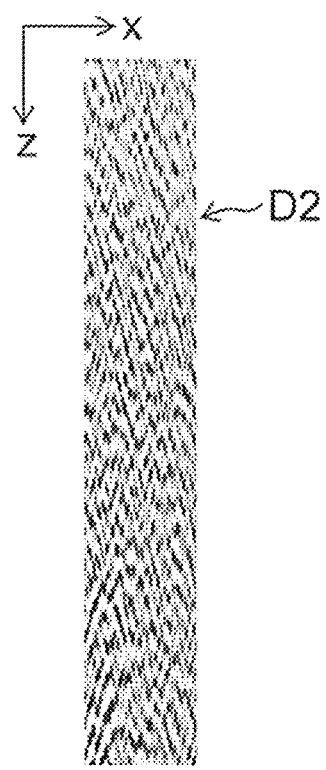
FIG. 10C is a diagram to describe a determination method of the quality of the element data.

FIGS. 10A to 10C are diagrams to describe a method of calculating the quality of element data by correlation operation with the parabola. In FIGS. 10A to 10C, an X axis shows a channel position (scan direction) of element data and a Z axis shows an ultrasonic reception time corresponding to a depth direction or a depth of the subject OBJ.

Element data is ideally expected to become a parabolic shape with respect to a transmission aperture channel as a center. Therefore, a correlation between parabola C1 as illustrated in FIG. 10A and element data received by the ultrasonic probe 18 is calculated to acquire a correlation value, and this correlation value can be assumed to be a parameter showing the quality of the element data.

Since element data D1 illustrated in FIG. 10B has a higher correlation value with the parabolas C1, in a case where the correlation value is equal to or greater than a threshold, it is determined that the quality is high in step S40. Since element data D2 illustrated in FIG. 10C has a lower correlation value with the parabolas C1, in a case where the correlation value is less than the threshold, it is determined that the quality is low in step S40.

According to the present embodiment, element data in which the waveform of an ultrasonic reception signal largely collapses and the quality is considered to be low (for example, an image generated based on the element data or the one in which the accuracy of the determination result of sound velocity based on the element data is considered to be low) is excluded from a preservation object. By this means, it is possible to effectively reduce the capacity of a memory required to preserve element data before beam forming.

Here, it is also possible to perform the limitation of the numerical aperture of the element data in the first embodiment together with the limitation of the sample number of the element data in the depth direction of the subject in the second and third embodiments. By this means, it is possible to further reduce the data amount of the element data to be preserved.

Moreover, an example has been described where the ultrasonic transducers (elements 20) are one-dimensionally disposed in each above-mentioned embodiment, but the presently disclosed subject matter is not limited to this. For example, each above-mentioned embodiment is applicable to a case where the ultrasonic transducers are two-dimensionally disposed or a case where the ultrasonic transducers are disposed in an arbitrary curved shape instead of a plane shape (for example, a convex shape of convexity with respect to the subject OBJ).

What is claimed is:
1. An ultrasonic signal processing device comprising:
an ultrasonic probe including multiple elements configured to transmit an ultrasonic wave to a subject, receive an ultrasonic wave reflected by the subject and output an ultrasonic detection signal; and
a processor configured to:
  acquire pieces of element data output from each element,
  determine element data to be preserved, according to depth information on a reception echo at an acquisition time of the element data, among the acquired pieces of element data of each element, waveforms of the ultrasonic wave transmitted from the ultrasonic probe and waveforms of the acquired pieces of element data,
  preserve the element data determined to be preserved, and
  generate an image by processing the preserved element data.
2. The ultrasonic signal processing device according to claim 1, wherein
the processor limits at least one of a numerical aperture of the element data to be preserved and a sample number in a depth direction of the element data to be preserved, according to the depth information on the reception echo at the acquisition time of the element data.

3. The ultrasonic signal processing device according to claim 1, wherein
the processor increases a numerical aperture of the element data to be preserved as a depth of the reception echo at the acquisition time of the element data becomes deeper.

4. The ultrasonic signal processing device according to claim 1, wherein
the processor sets a numerical aperture of the element data to be preserved such that an F value: $F=L/x$ defined by a depth L of the reception echo and an aperture size x of the element data to be preserved becomes constant.

5. The ultrasonic signal processing device according to claim 1, wherein
the processor decreases a sample number of the element data to be preserved as a depth of the reception echo at the acquisition time of the element data becomes deeper.

6. The ultrasonic signal processing device according to claim 1, wherein
the processor narrows a range in a depth direction of the element data to be preserved as a depth of the reception echo at the acquisition time of the element data becomes deeper.

7. The ultrasonic signal processing device according to claim 1, wherein
the processor is further configured to determine the element data to be preserved, according to a difference between
a waveform of an ultrasonic beam transmitted when the element data is acquired and
a waveform of an ultrasonic reception signal after a reception focus or phase matching addition of the element data.

8. The ultrasonic signal processing device according to claim 1, wherein
the processor is further configured to determine the element data to be preserved, according to a correlation value calculated between the element data and a parabolic form.

9. A control method of an ultrasonic processing device, the control method comprising:
acquiring pieces of element data output from each element included in an ultrasonic probe including multiple elements configured to transmit an ultrasonic wave to a subject, receive an ultrasonic wave reflected by the subject and output an ultrasonic detection signal;
determining element data to be preserved, according to depth information on a reception echo at an acquisition time of the element data, among the acquired pieces of element data of each element; waveforms of the ultrasonic wave transmitted from the ultrasonic probe and waveforms of the acquired pieces of element data,
preserving the element data determined to be preserved, and
generating an image by processing the preserved element data.

10. The control method according to claim 9, wherein, according to the depth information on the reception echo at the acquisition time of the element data, at least one of a numerical aperture of the element data to be preserved and a sample number in a depth direction of the element data to be preserved is limited.

11. The control method according to claim 9, wherein
a numerical aperture of the element data to be preserved is increased as a depth of the reception echo at the acquisition time of the element data becomes deeper.

12. The control method according to claim 9, wherein
a numerical aperture of the element data to be preserved is set such that an F value: $F=L/x$ defined by a depth L of the reception echo and an aperture size x of the element data to be preserved becomes constant.

13. The control method according to claim 9, wherein
a sample number of the element data to be preserved is decreased as a depth of the reception echo at the acquisition time of the element data becomes deeper.

14. The control method according to claim 9, wherein
a range in a depth direction of the element data to be preserved is narrowed as a depth of the reception echo at the acquisition time of the element data becomes deeper.

* * * * *